US00PP19247P3

(12) United States Plant Patent van Kleinwee

(10) Patent No.: US PP19,247 P3

(45) Date of Patent: Sep. 16, 2008

(54) *GERANIUM* PLANT NAMED 'ZOLBRISCALA'

(50) Latin Name: *Pelargonium zonale (L.) L'Herit. ex Ait*
Varietal Denomination: Zolbriscala

(75) Inventor: Theodorus Cornelis Maria van Kleinwee, Hoorn (NL)

(73) Assignee: Syngenta Seeds B.V., Enkhuizen (NL)

( * ) Notice: Subject to any disclaimer, the term of this patent is extended or adjusted under 35 U.S.C. 154(b) by 0 days.

(21) Appl. No.: 11/605,580

(22) Filed: Nov. 29, 2006

(65) Prior Publication Data

US 2008/0127390 P1 May 29, 2008

(51) Int. Cl.
*A01H 5/00* (2006.01)

(52) U.S. Cl. ..... Plt./330

(58) Field of Classification Search ..... Plt./330
See application file for complete search history.

(56) References Cited

PUBLICATIONS

UPOVROM Plant Variety PBR 20051212 search for cultivar Zolbriscala.*

* cited by examiner

*Primary Examiner*—Annette H Para
(74) *Attorney, Agent, or Firm*—S. Matthew Edwards

(57) ABSTRACT

A new *Geranium* plant, particularly distinguished by the deep scarlet flower color, dark green foliage, very good round plant structure with good branching, and compact plant habit.

1 Drawing Sheet

Latin name of the genus and species of the plant claimed: *Pelargonium zonale* (*L.*) *L'Hérit. ex Ait.*
Varietal denomination: 'Zolbriscala'.

BACKGROUND OF THE NEW PLANT

The present invention comprises a new *Geranium,* botanically known as *Pelargonium zonale* (*L.*) *L'Hérit. ex Ait,* and hereinafter referred to by the variety name 'Zolbriscala'.

'Zolbriscala' is a product of a planned breeding program. The new cultivar 'Zolbriscala' has large, semi-double flowers, is relatively vigorous, but with a well-branched growth habit, and has good heat resistance.

'Zolbriscala' originates from a hybridization in a controlled breeding program in Enkhuizen, The Netherlands. The female parent was an unpatented hybrid seedling identified as 'J2295-2' with deep scarlet flower color, dark green foliage with slight zone, and not very vigorous. The male parent of 'Zolbriscala' was an unpatented hybrid seedling identified as 'J2278-4' with deep scarlet color, very vigorous, and long flower stem.

'Zolbriscala' was selected as one flowering plant within the progeny of the stated cross in 2000 in a controlled environment in Enkhuizen, The Netherlands.

The first act of asexual reproduction of 'Zolbriscala' was accomplished when vegetative cuttings were taken from the initial selection in the Fall of 2000 in a controlled environment in Enkhuizen, The Netherlands.

Horticultural examination of plants grown from cuttings of the plant initiated in April of 2001 in Enkhuizen, The Netherlands, and continuing thereafter, has demonstrated that the combination of characteristics as herein disclosed for 'Zolbriscala' are firmly fixed and are retained through successive generations of asexual reproduction. 'Zolbriscala' has not been observed under all possible environmental conditions. The phenotype may vary significantly with variations in environment such as temperatures, light intensity and day length.

BRIEF DESCRIPTION OF THE NEW VARIETY

The accompanying photographic drawing shows typical flower and foliage characteristics of 'Zolbriscala' with colors being as true as possible with an illustration of this type. The photographic drawing shows a flowering potted plant of the new variety.

DETAILED BOTANICAL DESCRIPTION

The measurements were taken in Enkhuizen, Netherlands, in August 2005 on 26 week old plants that were growing in window boxes. Culture of these plants started mid February, 2005 in the greenhouse; plants were transferred to window boxes mid May, 2005.

BRIEF SUMMARY OF INVENTION

The following observations, measurements, and comparisons describe plants grown outside in Enkhuizen, The Netherlands. The following traits have been repeatedly observed and are determined to be basic characteristics of the new variety. The combination of these characteristics distinguishes this *Geranium* as a new and distinct variety.

Color references are primarily to the R.H.S. Colour Chart of The Royal Horticultural Society of London.

Plants of the new *Geranium* differ primarily form the plants of the female parent 'J2295-2' in the following characteristics:

The plants of the female parent 'J2295-2' have a deeper scarlet flower color, darker green foliage with more zoning, and are less vigorous than plants of the new *Geranium.*

Plants of the new *Geranium* differ primarily from the plants of the male parent 'J2278-4' in the following characteristics:

The plants of the male parent 'J2278-4' are almost single flowered, are more vigorous, have a lighter green foliage, and a longer flower stem than plants of the new *Geranium.*

TABLE 1

DIFFERENCES BETWEEN THE NEW VARIETY 'ZOLBRISCALA' AND A SIMILAR VARIETY

| | 'Zolbriscala' | 'Fisrocky Dark Red' (U.S. Plant Pat. No. 12,237) |
|---|---|---|
| Leaf zoning | Weak zoning | Strong zoning |
| Flower color (upper side of upper petal) | 44A | 40A |
| Leaf color (upper side) | 139A | 137A |

Plant:
*Plant height* (*cm*).—23.
*Plant height* (*inflorescence included*) (*cm*).—34.
*Plant width* (*cm*).—35.
*Plant shape.*—Round.

Foliage:
*Length* (*cm*).—6.
*Width* (*cm*).—10.
*Shape.*—Reniform.
*Base shape.*—Cordate.
*Base size* (*cm*).—5.
*Apex shape.*—Very weak lobes.
*Apex size* (*cm*).—3.5.
*Color of upper surface.*—139A.
*Color of lower surface.*—137C.
*Color of zone.*—No zone.
*Color of veins.*—146A.
*Margin.*—Bicrenate.
*Petioles length* (*cm*).—5–9.
*Diameter of petiole* (*mm*).—3.
*Leaves smooth and hairy.*—Only at nerves.
*Texture of leaves.*—Upper surface smooth.
*Veins.*—Palmate.

Stem:
*Length of internodes* (*mm*).—15–45.
*Color of stem.*—146A.
*Diameter* (*mm*).—7.

Inflorescence:
*Shape.*—Round outline.
*Diameter* (*cm*).—11.
*Umbel depth* (*cm*).—5.
*Length of peduncle* (*cm*).—15–20.
*Peduncle diameter* (*mm*).—4–5.
*Color of peduncle.*—183B, with 146C spread over peduncle.
*Length of pedicel* (*cm*).—2.5–4.
*Color of pedicle.*—183A, with 146C spread over pedicel.
*Number of flowers per inflorescence.*—20.

Corolla:
*Form.*—Appears double.
*Shape.*—No round outline, fringled flower.
*Length of flower* (*cm*).—4.4.
*Width of flower* (*cm*).—3.9.
*Number of petals.*—5–6.
*Length of petals* (*upper/lower*) (*mm*).—Upper 25. Lower 23.
*Width of petals* (*upper/lower*) (*mm*).—Upper 21. Lower 21.
*Shape petals.*—Obovate, base acute, upper end is truncate or rounded, margin is entire.
*Color upper side of upper petals.*—44A.
*Color upper side of lower petals.*—44A.
*Color lower side of upper petals.*—43B, nerves 45C.
*Color lower side of lower petals.*—43B, nerves 45C.
*Number of petaloids.*—3; crumpled leaves.
*Color petaloids.*—44A.
*Fading color when flower starts aging.*—No.
*Duration of flowering.*—Continuous flowering throughout the Summer.

Bud (just before opening):
*Shape.*—Narrow elliptic.
*Shape base of bud.*—Truncate.
*Shape top of bud.*—Acuminate.
*Sepals hairy and smooth.*—Yes.
*Length* (*mm*).—8.
*Width* (*mm*).—5.
*Color.*—146B.
*Number of sepals.*—5.
*Color of sepals.*—146A.
*Length of sepals* (*mm*).—7.
*Width of sepals* (*mm*).—3.

Reproductive organs:
*Number of lobes of stigma.*—5.
*Color stigma.*—45A.
*Length of style* (*mm*).—4.
*Color of style.*—45D.
*Number of anthers.*—6–8.
*Length of anthers* (*mm*).—3.
*Shape of anthers.*—Ovate.
*Length filaments* (*mm*).—7.
*Color of filaments.*—155D, Top 44B.
*Pollen present.*—Yes.
*Color of pollen.*—32A.
*Fertility/seed set.*—No.

Seed development: No seed development has been observed on plants on the new *Geranium.*

Disease/pest resistance: No disease/pest resistance has been observed to date.

What is claimed is:

1. A new and distinct variety of *Geranium* plant, substantially as illustrated and described herein.

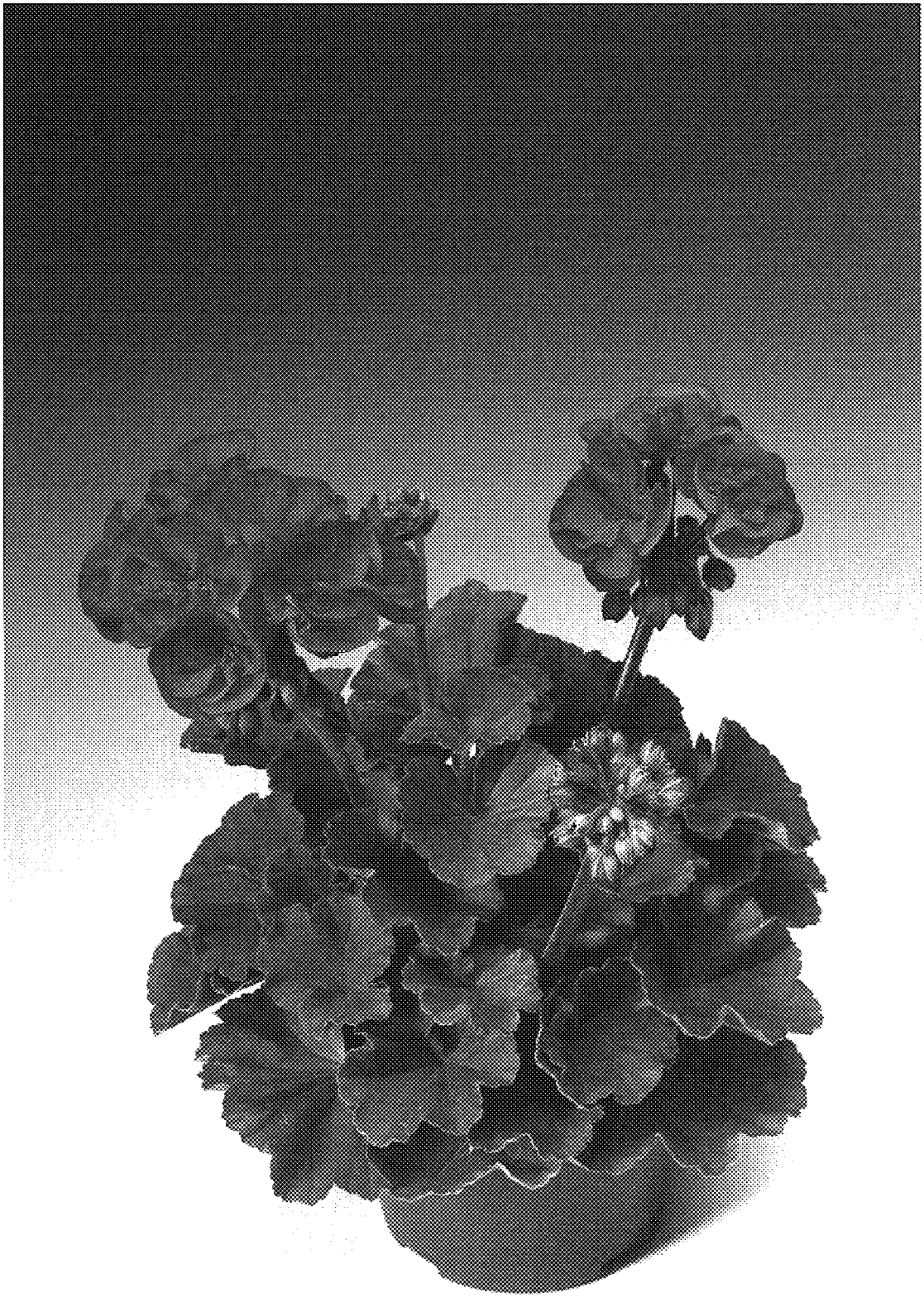

* * * * *